United States Patent
Shoher et al.

(10) Patent No.: US 6,641,397 B1
(45) Date of Patent: *Nov. 4, 2003

(54) METHOD OF FORMING A DENTAL COPING FROM LAMINATED METALLIC LAYERS IN A SINGLE HEAT TREATMENT

(76) Inventors: Itzhak Shoher, 56 Jehoshafat Street, Herzelia (IL), 46702; Aharon Whiteman, 13 J.L. Perez Petach, Tikvah (IL), 49206

( * ) Notice: Subject to any disclaimer, the term of this patent is extended or adjusted under 35 U.S.C. 154(b) by 0 days.

This patent is subject to a terminal disclaimer.

(21) Appl. No.: 09/602,319

(22) Filed: Jun. 23, 2000

Related U.S. Application Data

(63) Continuation-in-part of application No. 09/531,379, filed on Mar. 21, 2000.

(51) Int. Cl.⁷ .................................................. A61C 5/08
(52) U.S. Cl. ........................................ 433/223; 433/218
(58) Field of Search ................................. 433/206, 207, 433/218, 222.1, 223; 164/97; 419/2

(56) References Cited

U.S. PATENT DOCUMENTS

| | | | | |
|---|---|---|---|---|
| 4,676,751 A | * | 6/1987 | Shoher et al. | 433/222 |
| 4,742,861 A | * | 5/1988 | Shoher et al. | 164/80 |
| 4,940,637 A | * | 7/1990 | Shoher et al. | 428/607 |
| 5,234,343 A | * | 8/1993 | Shoher et al. | 433/215 |
| 5,336,091 A | * | 8/1994 | Shoher et al. | 433/215 |
| 5,593,305 A | * | 1/1997 | Shoher et al. | 433/218 |
| 5,730,600 A | * | 3/1998 | Shoher et al. | 433/223 |

* cited by examiner

*Primary Examiner*—Ralph A. Lewis

(57) ABSTRACT

A method for forming a dental coping from a base material composition containing high fusing temperature metal particles and a wax binder and a filler material composition containing low fusing temperature metal particles and a wax binder wherein the two materials are molded over the surface of a die either separately or as a laminate into a shape conforming to the shape of a tooth to be restored and heat treated in a a furnace in a single heat treatment operation from a temperature to cause the high fusing temperature metal particles to form a stable porous structure of high fusing temperature metal to an elevated temperature not to exceed about 1130° C. but preferably between about 1075° C. and 1100° C. so as to melt and densify the low fusing particles into the porous structure.

9 Claims, No Drawings

METHOD OF FORMING A DENTAL COPING FROM LAMINATED METALLIC LAYERS IN A SINGLE HEAT TREATMENT

This invention is a continuation-in-part of Ser. No. 09/531,379 filed Mar. 21, 2000 and relates to a method of forming a dental coping in a single heat treatment for use in the preparation of a dental restoration from two laminated metallic layers of different metal compositions.

FIELD OF THE INVENTION

Background of the Invention

A metal coping is used in dentistry in the construction of a dental crown and/or bridge. The metal coping functions as the under structure of the crown and is usually covered, for reasons of aesthetics, with a fired-on coating of a ceramic porcelain composition or a polymer based veneering material. The metal coping supports the coating and provides the required structural strength and rigidity for the restored tooth to resist the forces of mastication.

A metal coping may be cast from an investment of a wax or plastic pattern of the tooth to be restored. An alternative procedure which does not require waxing, investing or casting and which currently has been gaining wide acceptance by many laboratory practitioners and dentists is to form the coping from a moldable dental material composition composed of a mixture of high and low fusing temperature metal particles, as disclosed, for example, in U.S. Pat. No. 5,234,343 and U.S. Pat. No. 5,332,622 respectively. The dental material as taught in these patents, the disclosure of which is herein incorporated by reference, forms a porous structure upon heat treatment having a high void volume of above at least 20%. Before heat treatment the dental material is molded into the shape of the tooth to be restored. The molded shape is self-supported and is converted upon heat treatment in a dental furnace into a porous structure essentially any without shrinkage. The heat treatment temperature must be sufficient to entirely or substantially melt the low fusing temperature metal particles but rot the high fusing temperature metal particles. This results in the low fusing temperature metal particles interconnecting the high fusing temperature metal particles to form the porous structure without affecting the shape of the structure. The porous structure has a high void volume which is then filled to solidify the structure by adding a filler material of a metal or ceramic in a secondary heat treatment procedure.

In U.S. Pat. No. 5,593,305, the disclosure of which is herein incorporated by reference, it is further taught that the moldable dental material may be formed into a compacted strip formed of a base material of high and low fusing temperature metal particles and wax. Likewise the filler material may also be shaped into a compacted strip and composed of a composition of filler material and wax. The strip of base material is hand molded over the surface of a die and heat treated followed by a similar procedure for the strip of filler material in a secondary heat treatment operation.

SUMMARY OF THE INVENTION

It has been discovered in accordance with the present invention that a coping formed of two laminated metallic layers of high and low fusing temperature metal particle compositions can be heat treated in a dental furnace in a single operation with the heat treatment carried out gradually or in stages either manually or automatically. Heretofore, it was necessary to heat treat the base metallic layer of high fusing temperature metal particles separately to form an independent porous structure before adding filler material. The filler material was applied to the porous structure followed by a separate heat treatment operation to cause the porous structure to densify.

The method for forming a dental coping in accordance with the present invention comprises the steps of: forming a first sheet composed of a base material composition containing high fusing temperature metal particles and a wax binder; forming a second sheet of a filler material composition containing low fusing temperature metal particles and a wax binder, superimposing the two sheets to form a laminate, molding the sheets either separately or as a laminate over the surface of a die into the shape of a tooth to be restored, placing the molded laminate into a furnace and raising the temperature in the furnace from a temperature substantially below the melting temperature of the low temperature fusing particles to a maximum temperature not to exceed about 1075° C. The furnace temperature should preferably be raised gradually or in stages and over a time period sufficient to cause the high fusing temperature metal particles to form a stable porous structure of high fusing temperature metal before a temperature is reached in the furnace sufficient to melt and densify the low fusing particles in the porous structure.

DETAILED DESCRIPTION OF THE INVENTION

The present invention is an improvement over the teaching of U.S. Pat. No. 5,332,622 and is a variation of the teaching of copending application Ser. No. 09/531379 in that only two layers need be molded over the die either separately or as a laminate and fired in the dental furnace in a single heat treatment operation.

The base material layer comprises a metal composition formed of high fusing temperature metal particles and a volatile binder. The volatile binder is preferably a wax composition. The base material may be composed essentially of high fusing temperature metal particles and a binder or may be an aggregate mixture of high fusing temperature metal particles and low fusing temperature metal particles held together by the wax binder. The concentration of the binder may vary widely although preferably between about twenty percent by volume and up to eighty percent by volume of the base material composition. Any wax may be used which is relatively soft and tacky to form the binder and may be selected from any natural wax, mineral wax, or organic wax composition. The binder should melt relatively cleanly without leaving a significant residue at a melting temperature well below or at least no higher than the melting temperature of the low-fusing temperature metal particles.

The base material of high-fusing temperature metal particles may be selected from a single metal or metal alloy, preferably of precious metals such as platinum and palladium in any desired proportion relative to one another from zero to one hundred percent. Additional constituents may be added such as gold, silver, copper, magnesium, aluminum, zinc, gallium, indium and other metals selected from the third, fourth or fifth group of elements of the periodic table. The total weight percent of the elements other than gold, silver, and the platinum group metals should not exceed ten percent. Gold may be added in any proportion to the high-fusing temperature metal component to increase the affinity of the high-fusing temperature metal component to the low-fusing temperature metal components or to itself in the absence of other low fusing component. In the latter instance gold may represent a major constituent of the high fusing metal composition and depending upon its concentration may substantially lower the melting temperature of the high fusing component.

The filler material layer is composed primarily or entirely of low fusing temperature metal particles preferably of gold or a gold alloy, with gold as the major constituent. The preference for gold as the major constituent of the low-fusing layer is based on the known characteristics of gold in terms of its workability, biocompatibility, non-oxidizing properties and color. The filler material layer must possess a melting temperature below that of the high fusing temperature metal particles in the base material.

A dental coping is formedwhen the two layers are superimposed and molded over a die of the tooth to be restored, removed from the die and subjected to heat treatment in a dental furnace at a final temperature at least equal to the melting temperature of the low fusing temperature metal particles but below the melting temperature of the high fusing temperature metal particles in the base material composition. The wax binder is volatile and vaporizes at a temperature during heat treatment below the melting temperature of the low fusing temperature metal particles. The heat treatment can be conducted gradually or in stages of discreet temperature levels with the objective of causing the high fusing temperature metal particles to form a stable porous structure of high fusing temperature metal before raising the temperature in the furnace to a level sufficient to melt and densify the low fusing particles into the porous structure. When the two layers are superimposed and fired together as a laminate the temperature range can start as low as 50° C. and be raised to a maximum temperature not to exceed 1130° C. and preferably between 1075° C. and 1100° C. The temperature should be raised preferably at between 80–90° per minute although optimally held at the temperature of about 1030° C. for about 2–3 minutes.

During heat treatment the particles of the low fusing temperature metal layer must melt and diffuse into the base material layer. Moreover, this must occur without any shrinkage in the structure so that the final heat treated structure i.e., coping has a shape identical to the molded shape of the dental material before heat treatment. This is accomplished by controlling the firing temperature. However the thickness and binder concentration of each layer may also be adjusted to permit heat treatment in a single operation. If insufficient concentration of filler material exists the void volume of the base material will not be completely filled up during heat treatment leaving a structure which is still porous. Alternatively excess concentration of filler material is also undesirable.The concentration of filler material is varied by the thickness of the layer of filler material and the concentration of binder in the filler material layer.

It should be understood that the heat treatment operation can be performed adjusting the temperature in a staged sequence or gradually and can be controlled manually or automatically.

The technique of molding the dental material on a die is now conventional and taught in U.S. Pat. No. 5,730,600 the disclosure of which is herein incorporated by reference. The dental material may be of any desired geometry when molded over the die such as in the form of a strip.

It should further be understood that the dental material of the present invention although primarily intended for forming a dental coping may also be used for repair work or to join two restorations at the interproximal.

What is claimed:

1. A method for forming a dental coping comprising the steps of: forming a first sheet composed of a base material composition containing high fusing temperature metal particles and a wax binder; forming a second sheet of a filler material composition containing low fusing temperature metal particles and a wax binder, superimposing the two sheets to form a laminate, molding the sheets either separately or as a laminate over the surface of a die into the shape of a tooth to be restored, placing the molded laminate into a furnace and and performing a single heat treatment operation by raising the temperature in the furnace from a temperature substantially below the melting temperature of the low temperature fusing particles to a maximum temperature not to exceed about 1130° C. until a densified coping is formed.

2. A method for forming a dental coping as defined in claim 1 wherein the molded laminate is placed in the furnace with the temperature raised gradually over a temperature range and over a time period sufficient to cause the high fusing temperature metal particles to form a stable porous structure of high fusing temperature metal before allowing the temperature to reach a level sufficient to melt and densify the low fusing particles into the porous structure.

3. A method for forming a dental coping as defined in claim 2 wherein the temperature rise occurs in discreet steps.

4. A method for forming a dental coping as defined in claim 3 wherein the temperature of said heat treatment is held at an intermediate temperature of about 1030° C. for a time period longer than the resident time period at any lower temperature level.

5. A method for forming a dental coping as defined in claim 2 wherein the composition of each layer includes a volatile binder.

6. A method for forming a dental coping as defined in claim 5 wherein said volatile binder comprises wax.

7. A method for forming a dental coping as defined in claim 6 wherein said high-fusing temperature metal particles in said base material composition comprise precious metals and alloys thereof selected from the group consisting of platinum and palladium in a proportion relative to one another of from zero to 100% and at least one additional precious metal or alloy selected from the group consisting of gold, silver, copper, magnesium, aluminum, zinc, gallium, indium and other metals from the third, fourth or fifth group of elements of the periodic table.

8. A method for forming a dental coping as defined in claim 7 wherein said low-fusing temperature metal particles in said filler material composition comprises gold or a gold alloy as the predominant or at least major constituent thereof.

9. A method for forming a dental coping as defined in claim 8 wherein the filler material is sufficient in concentration by volume to diffuse into the base material layer upon said heat treatment.

* * * * *